United States Patent
Kollmitz et al.

(10) Patent No.: US 12,092,534 B2
(45) Date of Patent: Sep. 17, 2024

(54) TACTILE SENSOR INCLUDING A MEMORY WITH A CLASSIFICATION SCHEME AND METHOD FOR OPERATING A TACTILE SENSOR

(71) Applicant: Albert-Ludwigs-Universität Freiburg, Freiburg (DE)

(72) Inventors: Jan Kollmitz, Freiburg (DE); Matthias Kuhl, Freiburg (DE); Yiannos Manoli, Freiburg (DE)

(73) Assignee: Albert-Ludwigs-Universitaet Freiburg, Freiburg (DE)

( * ) Notice: Subject to any disclaimer, the term of this patent is extended or adjusted under 35 U.S.C. 154(b) by 294 days.

(21) Appl. No.: 17/622,043

(22) PCT Filed: Jun. 22, 2020

(86) PCT No.: PCT/EP2020/067362
§ 371 (c)(1),
(2) Date: Dec. 22, 2021

(87) PCT Pub. No.: WO2020/260205
PCT Pub. Date: Dec. 30, 2020

(65) Prior Publication Data
US 2022/0236120 A1    Jul. 28, 2022

(30) Foreign Application Priority Data
Jun. 24, 2019   (DE) .......................... 102019116923.2

(51) Int. Cl.
*G01L 1/18* (2006.01)
*G01L 1/20* (2006.01)
*G01L 5/162* (2020.01)

(52) U.S. Cl.
CPC ............... *G01L 1/18* (2013.01); *G01L 1/205* (2013.01); *G01L 5/162* (2013.01)

(58) Field of Classification Search
CPC . G01L 1/18; G01L 1/205; G01L 5/163; G01L 5/008
See application file for complete search history.

(56) References Cited

U.S. PATENT DOCUMENTS 4,633,099 A   12/1986   Tanabe et al.
5,760,530 A    6/1998   Kolesar
(Continued)

FOREIGN PATENT DOCUMENTS

CN       1735795 A     2/2006
CN    102589759 A     7/2012
(Continued)

OTHER PUBLICATIONS

Liu, H. et al. "A Computationally Fast Algorithm for Local Contact Shape and Pose Classification using a Tactile Array Sensor," 2012 IEEE International Conference on Robotics and Automation RiverCentre, Saint Paul, Minnesota, USA, May 14-18, 2012, 6 pages.

(Continued)

*Primary Examiner* — Tran M. Tran
(74) *Attorney, Agent, or Firm* — Slater Matsil, LLP

(57) ABSTRACT

In an embodiment a tactile sensor includes a plurality of stress sensors and at least one contact body, wherein the stress sensors are configured to detect a load pattern applied on a detection surface of the contact body.

9 Claims, 8 Drawing Sheets

(56) References Cited

U.S. PATENT DOCUMENTS

| | | | |
|---|---|---|---|
| 6,735,630 B1* | 5/2004 | Gelvin | B60R 25/33 709/200 |
| 6,812,621 B2* | 11/2004 | Scott | G06V 40/10 310/334 |
| 7,331,245 B2* | 2/2008 | Nishimura | G06F 3/04144 73/818 |
| 7,464,613 B2 | 12/2008 | Bieck et al. | |
| 8,127,623 B2* | 3/2012 | Son | G01L 1/146 73/862.046 |
| 8,272,278 B2* | 9/2012 | Loeb | G01L 5/228 374/45 |
| 8,327,721 B2* | 12/2012 | Bratkovski | G01B 7/28 73/862.046 |
| 8,707,796 B2* | 4/2014 | Duenas | G01L 1/2293 73/777 |
| 9,513,177 B2 | 12/2016 | Shalom et al. | |
| 9,910,964 B2 | 3/2018 | Burton et al. | |
| 10,172,560 B2* | 1/2019 | Schüttler | A61B 5/24 |
| 10,860,202 B2* | 12/2020 | Sepehr | G06F 3/0412 |
| 10,884,595 B2* | 1/2021 | Son | G06F 3/04847 |
| 11,026,600 B2* | 6/2021 | Lee | A61B 5/1123 |
| 11,269,509 B2* | 3/2022 | Sepehr | G06F 3/0412 |
| 11,300,397 B2* | 4/2022 | Kim | G01L 1/2231 |
| 11,507,267 B2* | 11/2022 | Sepehr | G06F 3/0488 |
| 11,537,850 B2* | 12/2022 | Hart | G06N 3/08 |
| 11,733,112 B2* | 8/2023 | Birchall | H03K 17/9625 715/773 |
| 11,809,672 B2 | 11/2023 | Rosenberg et al. | |
| 2005/0055145 A1 | 3/2005 | Bober et al. | |
| 2008/0134801 A1 | 6/2008 | Tseng et al. | |
| 2009/0031800 A1 | 2/2009 | Maekawa | |
| 2011/0241908 A1* | 10/2011 | Han | G08C 17/00 341/20 |
| 2013/0103703 A1* | 4/2013 | Han | G06F 16/164 707/755 |
| 2015/0233777 A1 | 8/2015 | Cadonau | |
| 2016/0025615 A1* | 1/2016 | Fishel | G01N 19/00 702/33 |
| 2020/0301510 A1* | 9/2020 | Birchfield | G06F 3/016 |
| 2021/0293643 A1* | 9/2021 | Correll | A61F 2/54 |
| 2022/0198227 A1* | 6/2022 | Sanz-Robinson | G06F 18/254 |

FOREIGN PATENT DOCUMENTS

| | | |
|---|---|---|
| CN | 105758563 A | 7/2016 |
| CN | 105934733 A | 9/2016 |
| CN | 106802200 A | 6/2017 |
| CN | 108680287 A | 10/2018 |
| DE | 102018211680 A1 | 1/2020 |
| EP | 3567529 A1 | 11/2019 |
| JP | S5995420 A | 6/1984 |
| JP | S6276785 A | 4/1987 |
| JP | H10178182 A | 6/1998 |
| JP | 3053102 U | 10/1998 |
| JP | 2005003670 A | 1/2005 |
| JP | 2005161450 A | 6/2005 |
| JP | 2006167814 A | 6/2006 |
| JP | 2013522588 A | 6/2013 |
| JP | 2017096782 A | 6/2017 |
| JP | 2018116054 A | 7/2018 |
| JP | 2018532436 A | 11/2018 |
| WO | 2018128513 A1 | 7/2018 |
| WO | 2018175662 A1 | 9/2018 |
| WO | 2019023309 A1 | 1/2019 |

OTHER PUBLICATIONS

Luo, S. et al. "Iterative Closest Labeled Point for Tactile Object Shape Recognition," 2016 IEEE/RSJ International Conference on Intelligent Robots and Systems (IROS) Daejeon Convention Center, Oct. 9-14, 2016, Daejeon, Korea, 6 pages.

Huaxiang Wang et al., "Principles and Applications of Tramsducers," Tianjin University Press, Mar. 2017, 16 pages.

Zeyuan Xu et al., "Modern Electronic Technology Tour," Science and Technology of China Press, Oct. 1986, 20 pages.

* cited by examiner

Fig. 16A
Fig. 16B
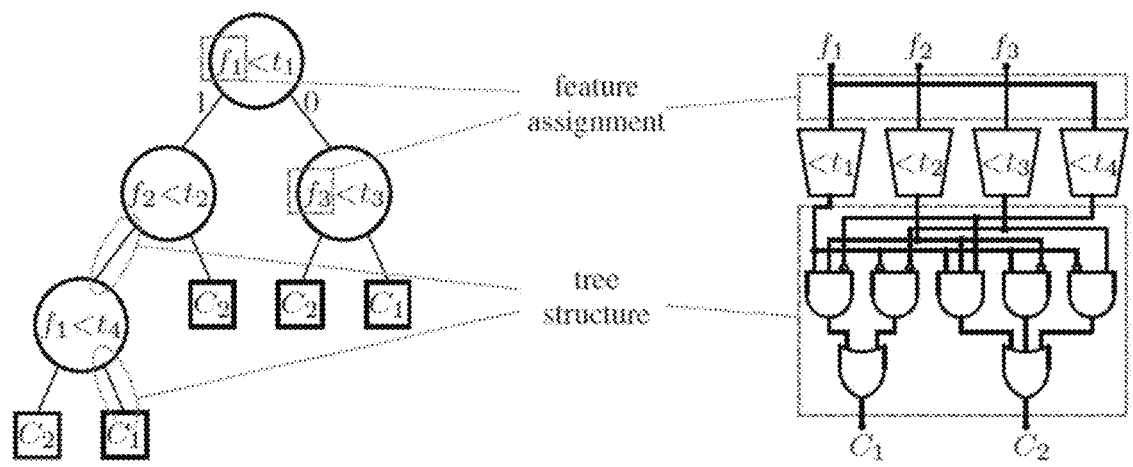
Fig. 16C
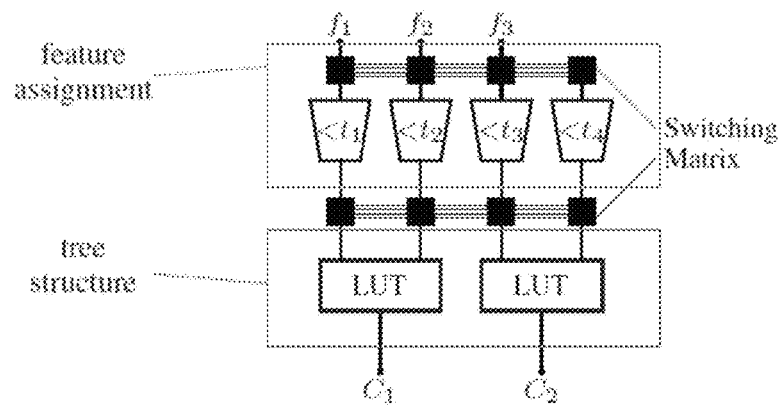

TACTILE SENSOR INCLUDING A MEMORY WITH A CLASSIFICATION SCHEME AND METHOD FOR OPERATING A TACTILE SENSOR

This patent application is a national phase filing under section 371 of PCT/EP2020/067362, filed Jun. 22, 2020, which claims the priority of German patent application 102019116923.2, filed Jun. 24, 2019, each of which is incorporated herein by reference in its entirety.

TECHNICAL FIELD

A tactile sensor is provided. Moreover, a method for operating a tactile sensor is provided.

SUMMARY

Embodiments provide a tactile sensor with improved speed and versatility. Further embodiments provide a method for operating a tactile sensor with improved speed and versatility.

The tactile sensor is a transducer, by means of which a load pattern on a detection surface of the tactile sensor is detectable. The load pattern may be caused by an object slipping along the detection surface, an object pressing statically against the detection surface or an object bouncing off the detection surface, or a mixture of said processes.

The tactile sensor comprises a plurality of stress sensors. The stress sensors may be arranged on a common substrate. In particular the stress sensors may have been fabricated in a common fabrication method, in particular in a C-MOS process. In particular, the stress sensors are integrated into a common chip. For example, the stress sensors may have been fabricated in a common fabrication process. The stress sensors may respectively consist of p-MOS and/or n-MOS transistors. For example, each stress sensor comprises four transistors which are connected as a Wheatstone bridge.

The tactile sensor comprises at least one contact body. The contact body may be a full body in which the stress sensors are embedded. In particular, a surface of the stress sensor which is sensitive to mechanical stress is completely covered by the contact body. For example, the contact body provides mechanical connection between the stress sensors and the object causing the load pattern.

The stress sensors are set up to detect static tactile forces and dynamic tactile forces applied on the detection surface of the contact body. In particular, the contact body transfers mechanical stress from its detection surface to the stress sensors. The stress sensors may be mechanically connected to a common contact body. In particular, the detection surface of the contact body is mechanically connected to all stress sensors of the contact body. Both, dynamic and static tactile forces may act perpendicularly or oblique with respect to the detection surface.

A static tactile force is a constant force acting on the detection surface. In this context, a constant force does not change in magnitude or direction over a first time span, wherein the first time span is at least hundred times, preferable at least thousand times, larger than the maximum sampling rate of the tactile sensor. For example the first time span is at least 0.5 seconds.

A dynamic tactile force is a varying force, acting on the detection surface. In this context, a varying force does change in magnitude and/or direction over a second time span, wherein the second time span is at least twice as large as the sampling rate of the tactile sensor. For example the second time span is at most five seconds, preferable at most 0.5 seconds.

For example, the dynamic tactile force varies with a frequency between 1 Hz and 1000 Hz. Advantageously, the detection of tactile forces between 1 Hz and 1000 Hz enables the detection of surface properties of an object slipping along the detection surface.

In particular, the dynamic tactile force varies with a frequency between 40 Hz and 400 Hz. Advantageously, the detection of dynamic tactile forces at frequencies between 40 Hz and 400 Hz enables detection of an object slipping along the detection surface.

The chip comprises a memory with a classification scheme, wherein the classification scheme assigns a set of output values of the plurality of stress sensors to a predefined load pattern.

The classification scheme is generated by means of a machine learning algorithm. The output of the machine learning algorithm is the classification scheme, which may be a decision tree ensemble algorithm. In particular, the classification scheme is a random forest algorithm.

Furthermore, a method for generating classification scheme is specified. With the method, in particular, classification scheme for a tactile sensor described here can be generated. Thus, all features disclosed for the tactile sensor are also disclosed for the method and vice versa.

For example the classification scheme is obtained by performing the following steps a) to c), also called training of the decision tree ensemble:

a) Predefine classes of load patterns. By predefining the classes of load patterns, it is predetermined which possible load patterns can be detected by means of the tactile sensor. Different classes of load patterns can be distinguished as an object sliding along the detection surface, bouncing off the detection surface or pressing against the detection surface. Additionally the different classes of load patterns can be distinguished by parameters like materials of the object, surface properties of the object, speed of the object slipping along the detection surface, pressure of the object against the detection surface.

b) Performing multiple representative measurements of each predefined class of load patterns with a reference tactile sensor. For example, load patterns of each predefined class of load patterns are measured at least 100 times, preferable at least 300 times. In this measurement each stress sensor provides an output value in response to the load pattern load pattern applied. The output value of the stress sensors may be electrical voltage values or electrical current values, wherein the voltage or current depends on the amount of stress sensed by each sensor respectively.

c) Defining a decision tree ensemble by assigning the sets of output values to each predefined class of load patterns respectively. In this context, a set of output values is the entirety of all output values of the plurality of stress sensors in response to a load pattern. After performing multiple representative measurements, multiple sets of output values are assigned to each class of load patterns.

The classification scheme, which is obtained by multiple measurements by means of a representative tactile sensor, is loaded in the memory of the tactile sensor. The classification scheme enables to assign a set of output values caused by a load pattern to one of the predefined classes of load patterns. Consequently, the predefined classes of load patterns are detected by means of the tactile sensor.

In particular, the classification scheme for the classification of load patterns resulting from static tactile forces and dynamic tactile forces is generated by the same method and by the same setup.

Furthermore, a method operating a tactile sensor is specified. With the method, in particular, a tactile sensor described here can be produced. Thus, all features disclosed for the tactile sensor are also disclosed for the method and vice versa.

The method for operating a tactile sensor comprising a contact body with a detection surface, a plurality of stress sensors and a chip comprises the following method steps:

applying a load patterns on the detection surface of the contact body;

transducing the load pattern to a set of output values by means of the stress sensors; and assigning the output values to a predefined class of load patterns by means of the chip and the classification scheme.

For example the detection surface is one or a multiplicity of surface of the contact body. In particular the detection surface is freely accessible. Thus, objects may get in direct contact with the contact body.

The load pattern may be caused by an object which makes direct contact with the detection surface. The load pattern may be a dynamic tactile force or a static tactile force, which is transferred through the contact body to the plurality of stress sensors. The stress sensors respectively return an output value in response to the load pattern.

The entirety of output values returned in response to the load pattern is a set of output values. The set of output values may be assigned by means of a decision tree ensemble to one of the predefined load pattern classes. The tactile sensor may return the predefined load pattern class to which the output values are assigned as being detected.

The load patterns result from static tactile forces and/or dynamic tactile force on the detection surface. Static tactile forces and dynamic tactile force on the detection surface are classified by means of the same classification scheme. In particular, the load patterns consist of a mixture of dynamic and static tactile forces. Both, dynamic and static tactile forces are classified by means of the same stress sensors and the same classification scheme. In particular, the load pattern is detected and classified without performing a spectral analysis of the output values.

BRIEF DESCRIPTION OF THE DRAWINGS

Further advantages and advantageous embodiments and further developments of the tactile sensor and the method for operating the tactile sensor will become apparent from the following exemplary embodiments illustrated in conjunction with the figures.

FIGS. 16A, 16B and 16C show exemplary implementation schemes of a decision tree ensemble utilized in a tactile sensor.

DETAILED DESCRIPTION OF ILLUSTRATIVE EMBODIMENTS

Figure 1:
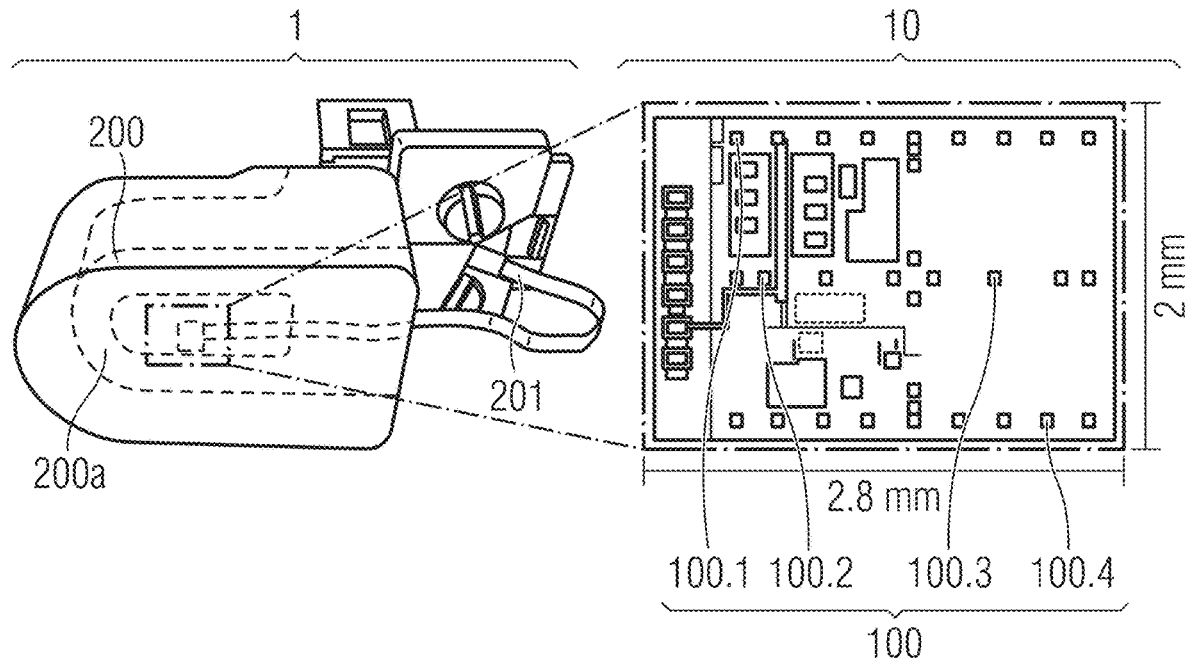
FIG. 1 shows an exemplary embodiment of a tactile sensor and a chip.

The same, similar or equivalent elements are provided in the figures with the same reference numerals. The figures and the proportions of the elements shown in the figures with each other are not to be considered to scale, unless units are expressly indicated. On the contrary, individual elements can be exaggerated in size for better presentation and/or better intelligibility.

FIG. 1 shows an exemplary embodiment of a tactile sensor 1 and an exemplary embodiment of a chip 10 utilized in a tactile sensor 1. The tactile sensor 1 comprises a contact body 200 into which the chip 10 is embedded. The mount 201 enables connecting the chip 10 electrically by means of a flex cable. In the present exemplary embodiment, the mount 201 is embedded in the contact body 200.

The chip 10 comprises multiple stress sensors 100.1, 100.2, 100.3, 100.4. The chip 10 comprises 32 stress sensors and all necessary readout circuitry. The chip is bonded onto a flexible flat cable for power supply and serial communication. Advantageously the chip is compact an easy to handle.

To form the tactile sensor 1, the chip 10 is embedded in the contact body 200 made of silicone (PDMS). The contact body 200 has the shape of a fingertip. Advantageously the chip does not require any additional electronic components and wiring.

Load patterns on the contact body 200, in particular the detection surface 200a, deform the contact body and induce stress profiles in the chip 10. The 32 stress sensors 100 are distributed over the chip area and allow measuring the stress distribution in the chip. The stress profiles are specific to direction and intensity of the load pattern.

A possible load pattern can be a dynamic tactile force, caused by an object 300 sliding along the detection surface 200a. The tactile sensor 1 is capable of measuring vibrations of up to 400 Hz, which is crucial for detecting such load pattern. Thus, the tactile sensor 1 has a sample rate of at least 960 Hz, in order to guarantees sufficient bandwidth. Since the stress distribution over the entire chip is measured, all 32 stress sensors are read, which reduces the sample rate to 30 Hz. The stress sensors are read serially, wherefore the vibration are still sampled with 960 Hz. Thus, the sample rate per stress sensor 100 corresponds to the sample rate per tactile sensor 1 divided by the number of stress sensors 100 per chip 10.

Vibrations are recorded at multiple points on the chip's 10 surface. The spatial distribution of the stress sensors 100 on the chip 10 has a neglectable effect on the measurement, as long as the wavelength of the vibrations measured is much larger than the distance of the stress sensors 100 on the chip 10. For example, the maximum distance of stress sensors 100 on the chip 10 is at least hundred times, preferably at least 1000 times, highly preferred at least 100000 times, smaller than the wavelength of a vibration to be measured.

Figure 2:
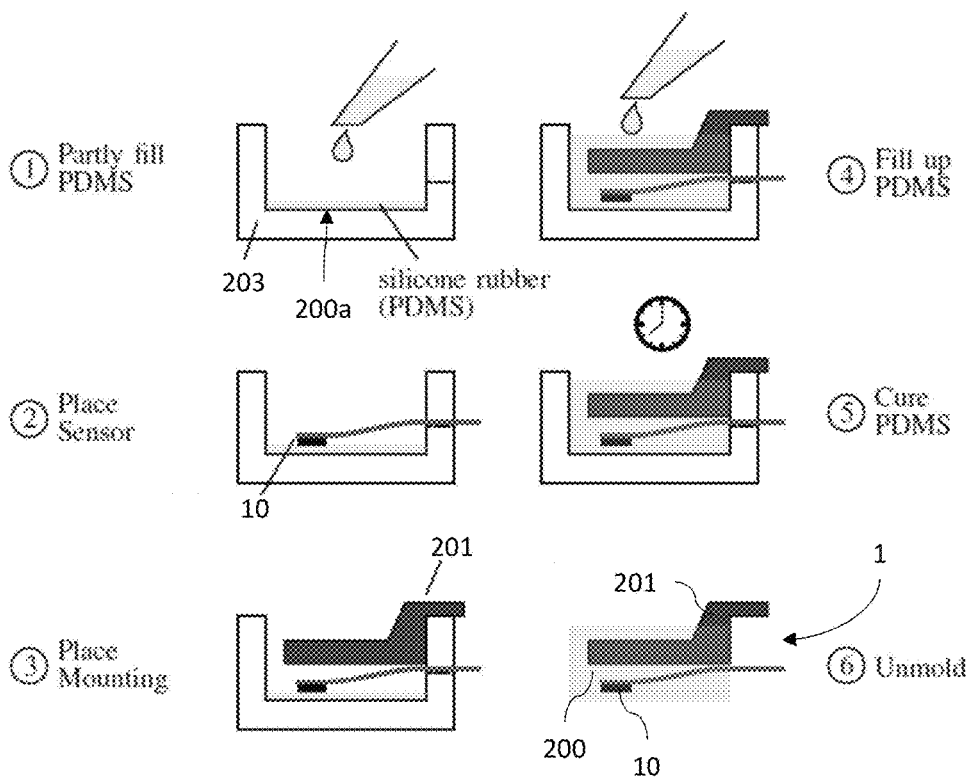
FIG. 2 shows an exemplary embodiment of a method for fabrication of a tactile sensor.

FIG. 2 shows an exemplary method for fabrication of a tactile sensor 1. In a first method step a mold 203 is filled with a first silicone layer. A bottom surface of the silicone layer, facing the mold 203, becomes the detection surface 200a of the tactile sensor 1.

In a second step, the chip 10 is placed flat on top of the first silicone layer, on a side facing away from the mold 203. The silicone has sufficient viscosity to hold the chip in place.

In a third method step the mounting 201 is fixed to the mold 203.

In a fourth method step the contact body 200 is completed, by filling up the mold with silicone material. In this method step the chip 10 is completely embedded into the contact body 200. The mount 201 is partially embedded into the contact body 200.

In a fifth method step the contact body 200 is cured at 2 bar pressure and 60° C. The contact body 200 is made of PDMS (Dowsil 3140). The PDMS material advantageously provides tight mechanical coupling between the stress sensors 100 and the contact body 200.

In a sixth method step the mold 203 is removed from the contact body 200. After removal of the mold 203, the detection surface 200a is freely accessible.

Figure 3A:
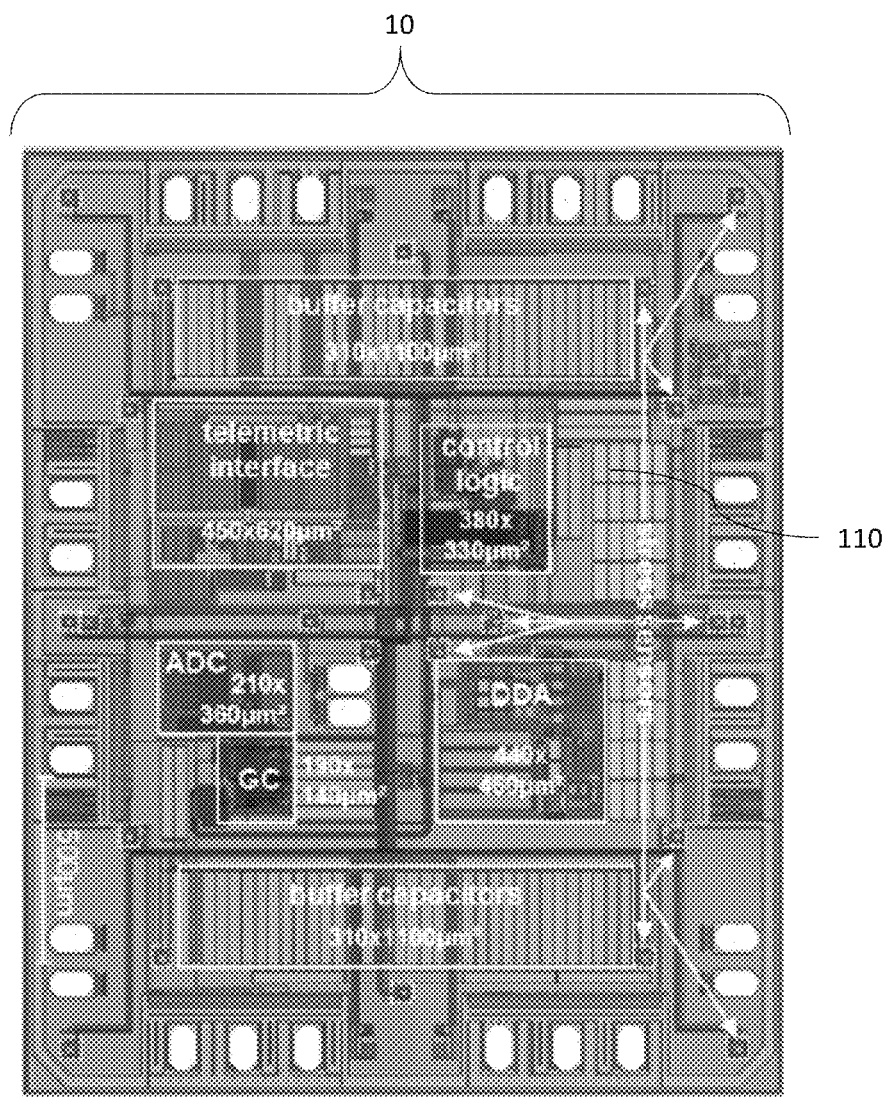
FIGS. 3A and 3B show an exemplary embodiment and a schematic embodiment of a chip used in a tactile sensor.
Figure 3B:
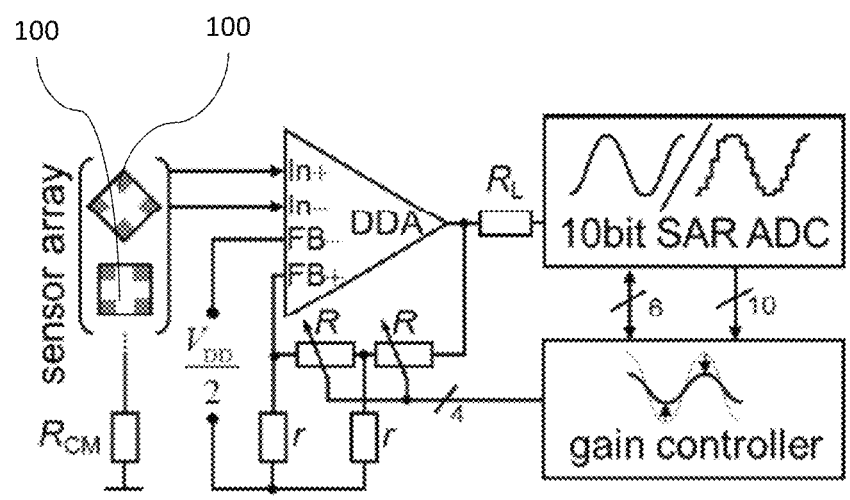

FIGS. 3A and 3B show a top view and a schematic view of an exemplary chip 10 utilized in a tactile sensor 1. The chip is fabricated in a 0.35-μm process. The chip 10 comprises 24 transistor-based stress sensors 100 for measuring either in-plane shear stress of the difference of in-plane normal stresses are strategically distributed over the chip area. The stress sensor signals are processed by a variable-gain differential difference amplifier and digitized by a 10-bit SAR ADC. The chip 10 has a resolution down to 11 kPa at highest gain.

The 24 stress sensors 100 are consecutively connected to the readout unit by a 5-bit multiplexer (MUX). The processed stress sensor 100 can be biased in four directions by an additional multiplexer, which enables an offset-compensated operation due to a Wheatstone bridge architecture of the stress sensors. A variable-gain differential difference amplifier (DDA) together with a 10-bit successive approximation (SAR) analog-to-digital converter (ADC) performs the stress sensor readout.

As shown in FIG. 3A, the chip 10 has an area of 2×2.5 mm^2.

The stress sensor 100 readout as shown in FIG. 3B is composed of a differential difference amplifier (DDA) with variable gain, followed by a SAR ADC and a gain controller (GC). Based on the digitized output value of the stress sensors, the gain controller determines the maximum ideal gain value with respect to the linear DDA output range on the basis of a binary tree search.

The architecture of the DDA offers one differential input pair for the stress sensors and a separate pair for the feedback. Thus, a high ohmic interface for the stress sensor connection is provided and impedance variations in the feedback path during gain variation are not influencing the load impedance of the stress sensor during readout.

Figure 4A:
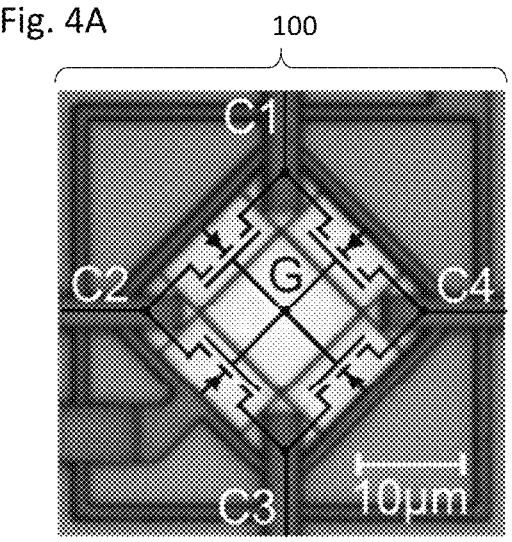
FIGS. 4A and 4B show exemplary embodiments of stress sensors used in a tactile sensor.
Figure 4B:
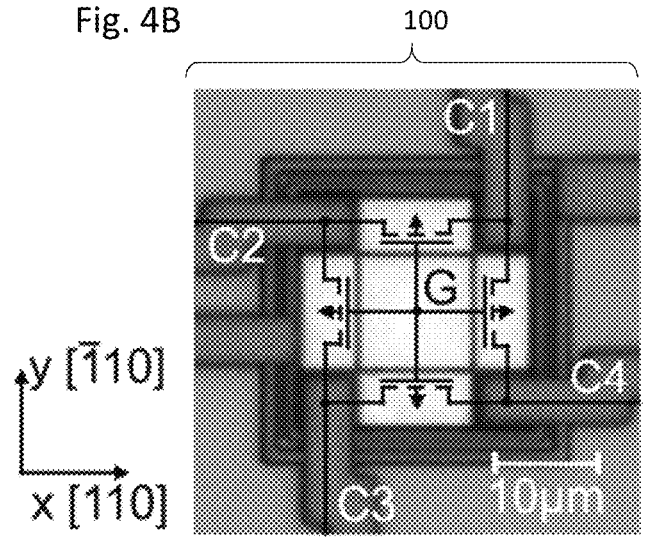

FIGS. 4A and 4B show a top view of stress sensors 100. Each of the stress sensors forms a square of active elements and can be described by four transistors in a Wheatstone bridge arrangement. The orientation is indicated by the coordinate system (x,y) parallel to the chip 10 edges. The doping polarity has as strong impact on the piezo resistive coefficients of MOS inversion layers. For instance $\Pi$ can be ten times higher in p-type than in n-type silicon, while $\Pi_{12}$ is nearly 50 times higher in the n-type silicon than in p-type silicon. The in plane shear stress is therefore measured by means of a NMOS type stress sensor 100 rotated by 45° with respect to (x,y). The PMOS type stress sensor is oriented parallel to the coordinate system. Thus, the PMOS type stress sensor is sensitive to the difference of in-plane normal stresses. All four transistors within each stress sensor have a W/L ratio of 5 μm/10 μm. These dimensions represent a good compromise between four main sensor characteristics.

Each NMOS stress sensor is activated by connecting the common gate of its transistor to the drain voltage. Each PMOS stress sensor is activated by connecting the common gate of its transistor to the source voltage. The power consumption of the overall system thus can be reduced, as only the processed sensor is activated temporarily.

Figure 5:
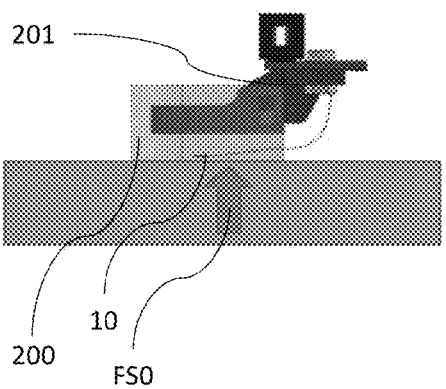
FIGS. 5, 6 and 9 show exemplary embodiments of tactile sensors onto which a load pattern is applied.
Figure 6:
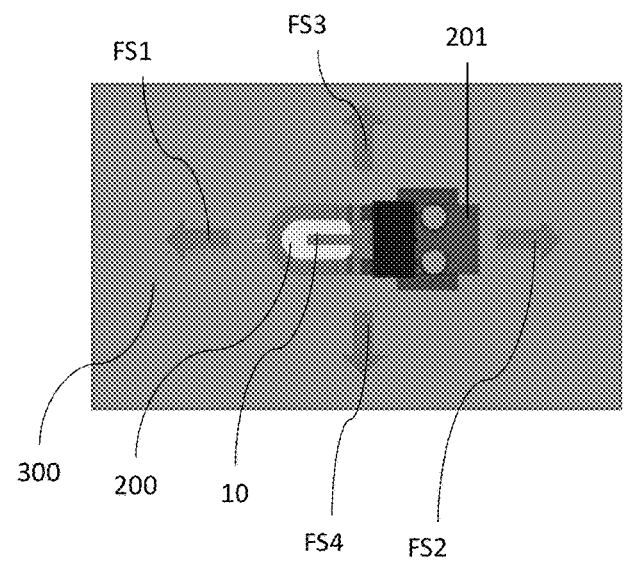

FIGS. 5 and 6 show schematic side view and a top view of the tactile sensor 1 according to an exemplary embodiment. The tactile sensor 1 comprises a detection surface 200a, which is in direct contact to the object 300. A perpendicular static tactile force $FS_0$, a forward static tactile force $FS_1$, a backward static tactile force $FS_2$ and sideward static tactile forces $FS_4$, $FS_3$ between the object 300 and the tactile sensor 1 are detectable load patterns.

Figure 7:
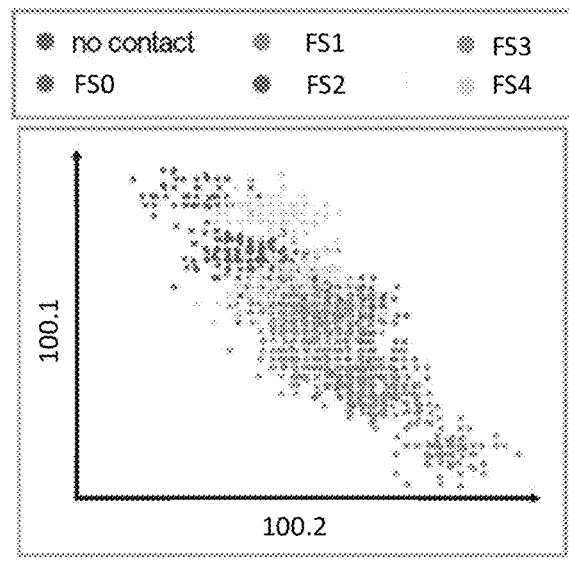
FIGS. 7 and 8 show scatter plots of output values of exemplary stress sensors.
Figure 8:
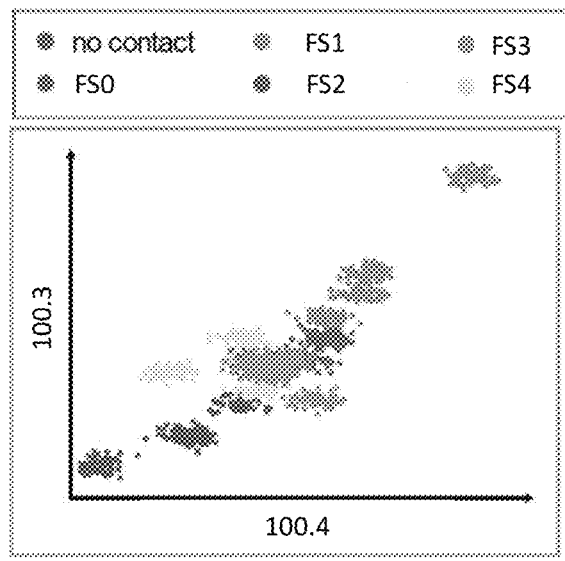

FIGS. 7 and 8 show measurement results of load patters with static tactile forces in different directions as a scatter plot for four stress sensors. For this measurement class data is utilized to assign a measured set of output values to a predefined class of load patterns. Each point in the scatter plot represents on scatter sample and is color coded according to the load class it is assigned to.

Reference data, which is labeled "no contact", is collected without any mechanical contact between the object 300 and the contact body 200. Data with pure normal static tactile force is labeled $FS_0$. In addition to the normal static tactile force tangential static forces are applied by gradually moving the object 300 under the tactile sensor 1. The data is labeled $FS_1$, $FS_2$, $FS_3$ and $FS_4$ according to the corresponding direction shown in FIGS. 5 and 6.

The Classification scheme, in particular a decision tree ensemble, is trained to detect contact and classify the load pattern caused by the shear forces in different directions.

Depending on the stress sensor, some classes of load pattern result in similar output values of the stress sensor. However, the entirety output values, the set of output values, is distinguishable for different load patterns. The classification scheme considers the entire set of output values, whereby the applied load pattern is reliably assigned to a predefined class of load patterns. A trained random forest algorithm may assign the load patterns to the correct class of load patterns with 99.8% accuracy.

Figure 9:
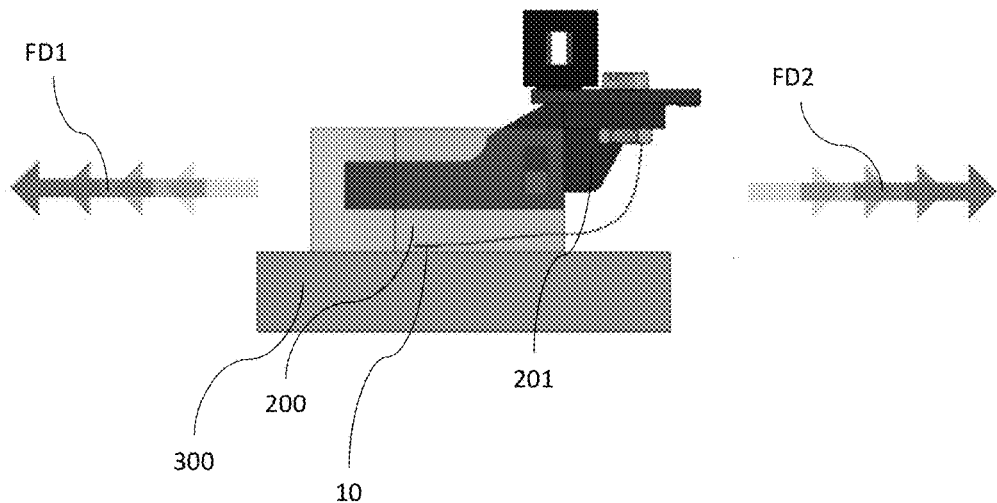

Furthermore, as shown in FIG. 9, a class of load patterns may be defined as the tactile sensor 1 sliding with its detection surface 200a along the object 300. The detection surface 200a may have a surface structure with multiple parallel ridges. The ridges cause a vibration of the contact body 200, when the object 300 slides along the detection surface 200a. Detection of the vibration enables to distinguish static tactile forces from dynamic tactile forces.

Figure 15:
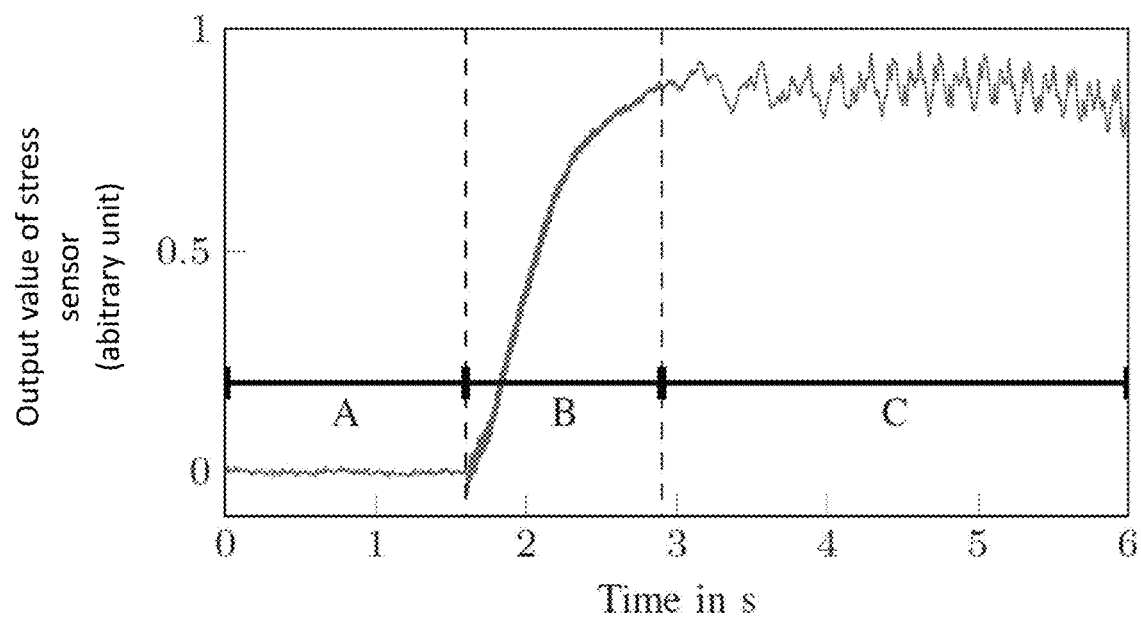
FIG. 15 shows an exemplary output value of a single stress sensor for different load patterns.

By measuring the vibration by means of a single stress sensor of the chip 10 at a sample rate of 960 Hz, it is possible to preclude, that the entire vibration is damped by the contact body. FIG. 15 shows the sensor output at three different states A, B and C. In state A the tactile sensor 1 does not move relatively to the object 300. However, in state A solely a static tactile force perpendicularly to the detection surface is present. In state B the tangential force is increased until the object 300 slides along the detection surface 200a.

Figure 10:
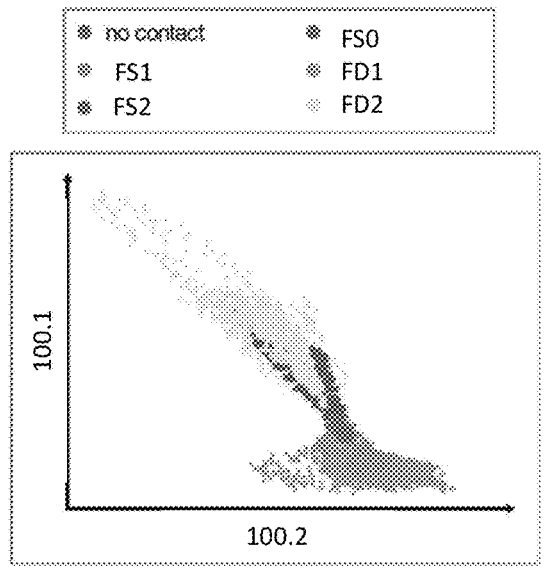
FIG. 10 shows scatter plots of the output values of exemplary stress sensors in response to load patterns with static and dynamic tactile forces.

In state C the object 300 slips with 10 mm/s along the detection surface 200a and causes an oscillating output value of the stress sensor 100. Thus the dynamic tactile force can easily be detected by spectral analysis of the output value of a single sensor By analyzing the output of multiple stress sensors 100, in particular all 32 stress sensors, both load pattern of static and dynamic tactile forces may be detected, without spectral analysis. FIG. 10 shows the complete classification scheme as a scatter plot for the two most significant stress sensors 100. Each point in the scatter plot represents one sensor sample and is color-coded according to the predefined load class assigned to the respective output value. The random forest classification algorithm is trained with at least 50 trees and unconstrained tree growth. The 5-fold cross-validation results in a total accuracy of 99.6%. Each class of load pattern reaches a true-positive rate of a least 98%.

There is no sensor dimension in which the set of output values in response to static tactile forces and dynamic tactile forces do not overlap. Thus, it is not trivial to reliably classify a load pattern by means of one or two stress sensors. A dynamic tactile force may only be classified by the relation output values of multiple stress sensors.

Figure 12:
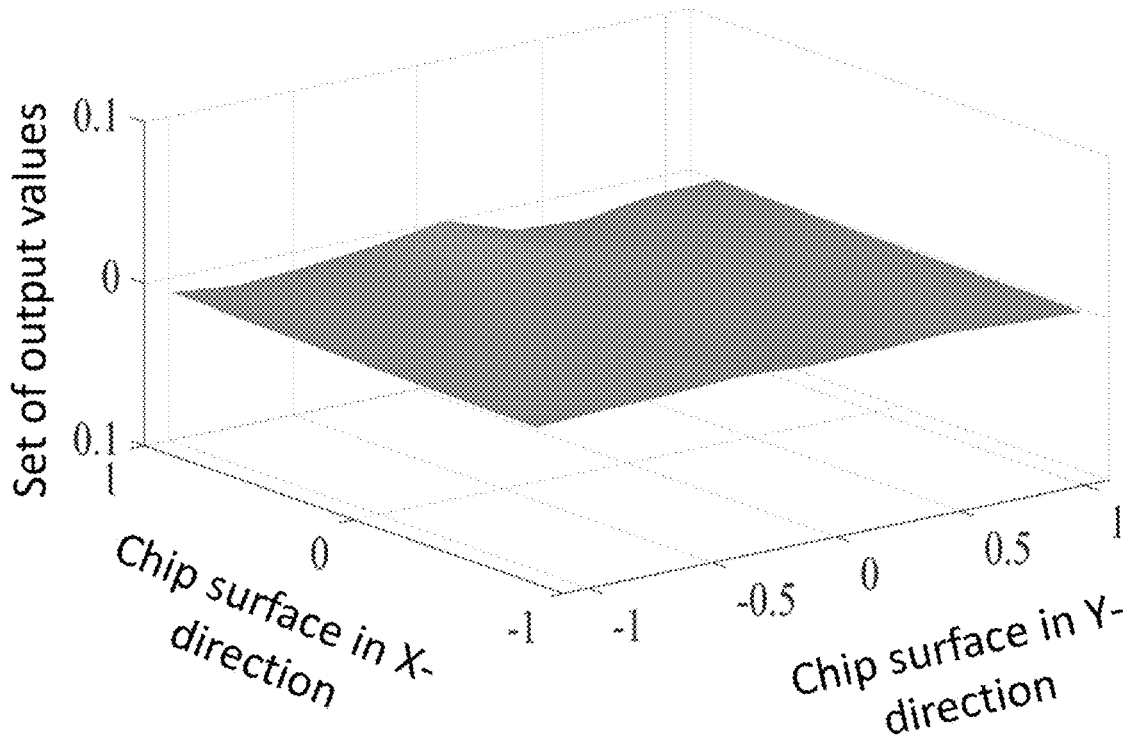
FIGS. 12 and 13 show a 3D-plot of exemplary output value sets with respect to the chip surface.
Figure 13:
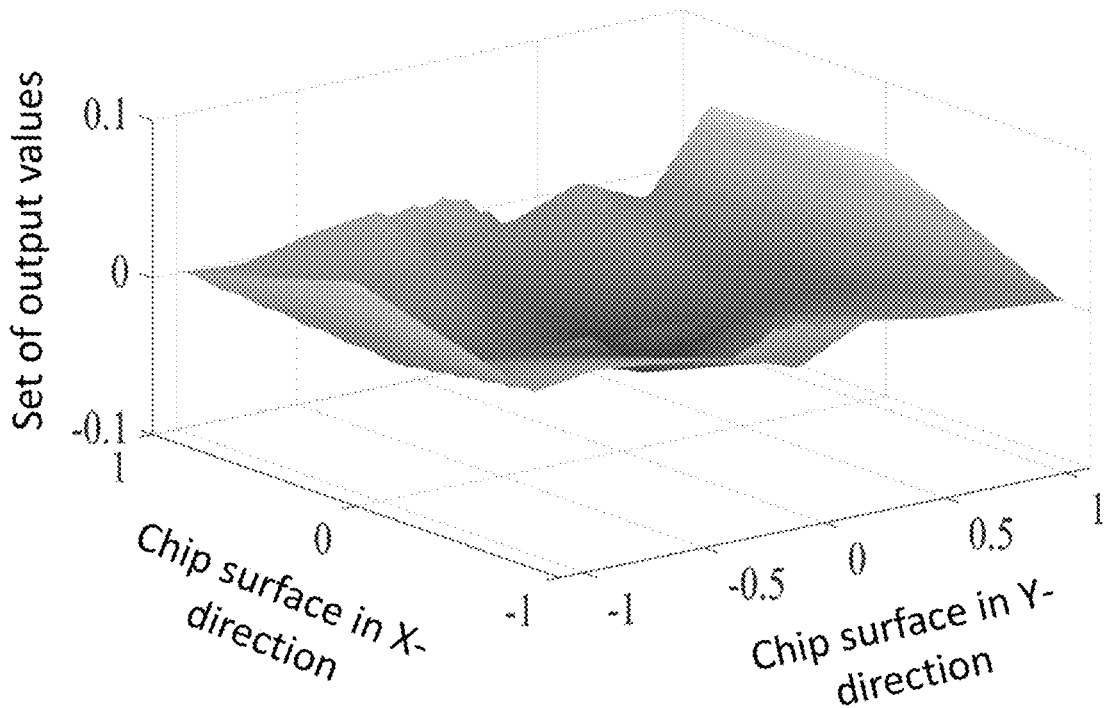

FIG. 12 shows a 3D-plot that visualizes output values of the stress sensors 100 over the chip 10 surface during static tactile force as load pattern. FIG. 13 shows a 3D-plot that shows output values of the stress sensors 100 over the chip 10 surface during dynamic tactile force as load pattern. For this visualization, the data is high-pass filtered to suppress any offset patterns from directional static force. Deviations from flat surface in the static plot are due to sensor noise. Hence, static tactile forces lead to well-defined stress patterns that can be distinguished from the distorted patterns in the slip sample. By training the classification algorithm may learn to distinguish these to patterns as two different classes of load patterns, whereby dynamic and static tactile forces are detectable by means of the same algorithm.

Figure 11:
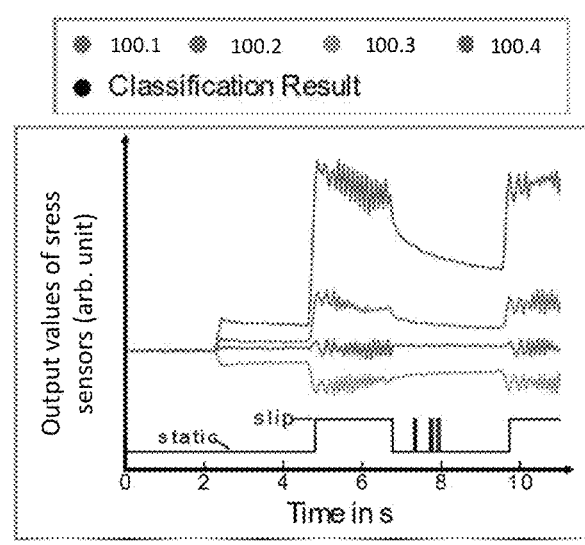
FIG. 11 shows the output value of exemplary stress sensors and the classification which results from these output values.

FIG. 11 shows a time domain measurement with the plurality of stress sensors 100 to validate the classification in a visual manner. The output values of four stress sensors are shown during the following load patterns: pure static normal tactile force $FS_0$, static tangential tactile force $FS_1$ or $FS_2$, forward dynamic tactile force $FD_1$. The order in the shown measurement is pure normal force for 2.5 seconds in the beginning of the measurement, static forward force is increased until 4.7 seconds of the measurement, the object slides along the detection surface 200a until 6.8 seconds, the sliding motion stops until 9.5 seconds, the sliding motion of the object along the detection surface 200a start again. The plot also shows the classification result for each sensor sample.

Whenever a sliding motion causes a vibration of the contact body 200. The vibration results in oscillating signals of the stress sensors. The classification scheme allows to detect and correctly classify the load pattern of the sliding motion mostly correct and reacts very fast to the sliding motion.

Figure 14:
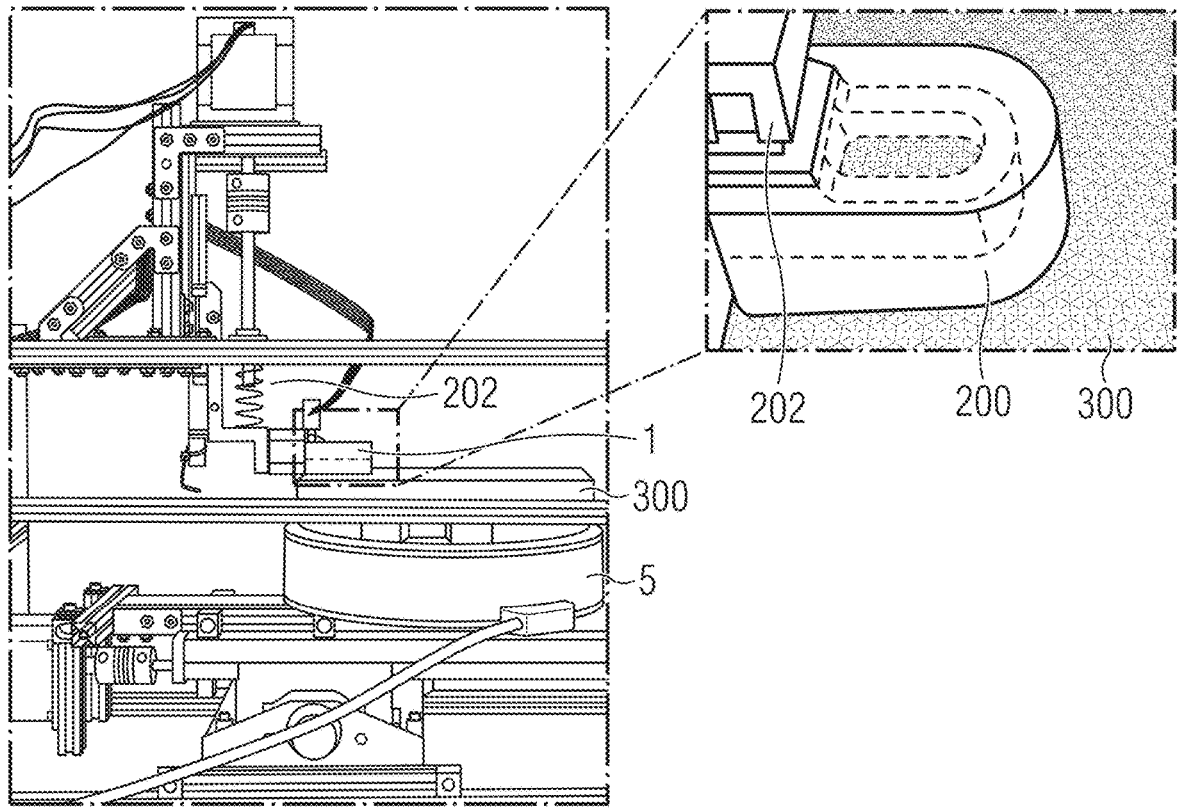
FIG. 14 shows an exemplary measurement setup for generating the classification scheme.

FIG. 14 shows a setup by means of which the classification scheme is generated. The setup comprises a classification mount 202 onto which the tactile sensor 1 is attached. By means of the classification mount 202 the tactile sensor is pushed against an object 300 with a definable normal tactile force $FS_0$. The object 300 is a 3D-printed plate with different surface patterns. The surface patterns can be smooth, ridged, circles or triangles. The surface pattern allows to generalize the classification scheme from the surface. Otherwise the classification algorithm would be limited to classify load patterns of objects with only one specific surface structure. The object 300 is mounted on an X-Y-cross table. The object 300 can be moved in parallel to the detection surface 200a by means of stepper motors. The steps are fine enough to gradually increase the tangential tactile force without sliding the tactile sensor over the object. The stepper motors can accelerate and move the table with up to 10 mm/s to create slip. The tangential force which is applied to the detection surface is recorded by a verification sensor 5.

When generating the classification scheme, a predefined load pattern is applied to the tactile sensor 1 and the corresponding output values are assigned to the predefined class of load patterns. Such measurement is repeated for multiple times, to generate a reliable decision tree ensemble.

FIG. 16A shows an example of a single decision tree after training. In this context, the training is the measurement of predefined load patterns and the assignment of the corresponding output values to the class of load patterns. The features $f_i$ and threshold values $t_i$ of the nodes, the class labels C, of the leafs, and the entire tree structure changes during training. In the context of the tactile sensor 1, the stress sensors 100.1, 100.2, 100.3, 100.4 correspond to features $f_1$, $f_2$, $f_3$, $f_4$, the thresholds $t_i$, correspond to output values of the stress sensors 100 and the classes C, correspond to predefined classes of load patterns.

FIG. 16B shows the static implementation in parts of a parallel architecture. In order to be able to continuously train the decision tree, the tree structure must remain reconfigurable.

As shown in FIG. 16C, the tree structure may be implemented by reconfigurable counter pails commonly used in FPGAs. The assignment of features to the nodes is achieved by a switching and interconnection network that wires the feature inputs to the appropriate node comparator. The Boolean function that encodes the tree structure and computes the leaf outputs is replaced by look-up-tables (LUTs) as used in FPGAs logic blocks. Only the comparators stay fixed and their thresholds must be stored in registers. This allows the architecture to support updates of the decision tree.

A full implementation of a decision tree ensemble comprises switching and interconnection blocks, which span the ensemble and allow comparators to be shared between trees. In particular, the trees of a decision tree ensemble may have different sizes.

The invention is not limited by the description based on the embodiments of these. Rather, the invention encompasses any novel feature as well as any combination of features, including in particular any combination of features in the claims, even if this feature or combination itself is not explicitly stated in the patent claims or exemplary embodiments.

The invention claimed is:
1. A tactile sensor comprising:
a chip comprising a plurality of stress sensors and a memory with a classification scheme; and
at least one contact body,
wherein the stress sensors are integrated into the chip and are distributed over an area of the chip,
wherein the stress sensors are configured to detect a load pattern applied on a detection surface of the contact body, and
wherein the classification scheme assigns a set of output values of the plurality of stress sensors to a predefined load pattern.

2. The tactile sensor according to claim 1,
wherein the load pattern comprises a static tactile force and/or a dynamic tactile force, and
wherein the dynamic tactile force varies with a frequency between 1 Hz and 1000 Hz, inclusive.

3. The tactile sensor according to claim 1, wherein the classification scheme is generated by a machine learning algorithm.

4. A method for operating a tactile sensor comprising a chip having a plurality of stress sensors and a memory with a classification scheme, and at least one contact body, wherein the stress sensors are integrated into the chip and are distributed over an area of the chip, the method comprising:
applying a load pattern to a detection surface of the contact body;
transducing, by the stress sensors, the load pattern to a set of output values; and
assigning, by the chip, the set of output values to a predefined class of load pattern by the classification scheme.

5. The method according to claim 4, wherein load patterns resulting from static and dynamic tactile forces on the detection surface are classified by the same classification scheme.

6. The method according to claim 4, wherein dynamic tactile forces are classified without spectral analysis of the output values.

7. A method for generating the classification scheme according to claim 4, the method comprising:
predefining classes of load patterns;
performing multiple representative measurements of each predefined class of load pattern with a reference tactile sensor; and
defining a decision tree ensemble by assigning sets of output values to each predefined class of load pattern respectively.

8. The method according to the claim 7, further comprising generating the classification scheme for a classification of load patterns resulting from static tactile forces and dynamic tactile forces.

9. A tactile sensor comprising:
a chip comprising a plurality of stress sensors and a memory with a classification scheme; and
at least one contact body,
wherein the stress sensors are integrated into the chip and are distributed over an area of the chip,
wherein the stress sensors are configured to detect a load pattern applied on a detection surface of the contact body,
wherein the stress sensors are transistor-based stress sensors and comprise a p-MOS transistor and an n-MOS transistor or p-MOS transistors and/or n-MOS transistors; and
wherein the classification scheme assigns a set of output values of the plurality of stress sensors to a predefined load pattern.

* * * * *